(12) United States Patent
Tyndall et al.

(10) Patent No.: US 7,381,244 B2
(45) Date of Patent: Jun. 3, 2008

(54) APPARATUS AND PROCESS FOR AIR CLEANING

(75) Inventors: Daniel Warren Tyndall, New Tripoli, PA (US); Timothy Christopher Golden, Allentown, PA (US); Thomas Stephen Farris, Bethlehem, PA (US); Fred William Taylor, Coplay, PA (US); Wayne Robert Furlan, Coopersburg, PA (US); John Joseph Rabasco, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 371 days.

(21) Appl. No.: 11/196,070

(22) Filed: Aug. 3, 2005

(65) Prior Publication Data

US 2007/0028770 A1    Feb. 8, 2007

(51) Int. Cl.
*B01D 53/04* (2006.01)
*G21F 9/12* (2006.01)

(52) U.S. Cl. .......................... 95/116; 95/143; 95/902; 588/14

(58) Field of Classification Search .................. 95/116, 95/117, 139, 140, 143, 902; 55/DIG. 9; 96/121, 132, 131, 153; 423/210, 219, 247, 423/249; 502/60, 79; 588/1, 2, 13–15
See application file for complete search history.

(56) References Cited

U.S. PATENT DOCUMENTS

| | | | |
|---|---|---|---|
| 3,430,418 A | 3/1969 | Wagner | |
| 3,564,816 A | 2/1971 | Batta | |
| 3,890,121 A * | 6/1975 | Thomas | ........................ 95/115 |
| 3,971,640 A | 7/1976 | Golovko | |
| 4,019,880 A | 4/1977 | Rabo et al. | |
| 4,369,048 A | 1/1983 | Pence | |
| 4,447,353 A | 5/1984 | Pence et al. | |
| 4,764,187 A | 8/1988 | Abrams | |
| 4,801,800 A | 1/1989 | Scheible | |
| 4,849,111 A | 7/1989 | Abrams | |
| 4,911,899 A | 3/1990 | Hagiwara et al. | |
| 4,975,575 A | 12/1990 | Perlman | |
| 5,106,759 A * | 4/1992 | Addison | ...................... 436/178 |
| 5,149,343 A * | 9/1992 | Sowinski | ...................... 95/127 |
| 5,174,800 A * | 12/1992 | Schwilling et al. | ........... 96/154 |
| 5,194,158 A * | 3/1993 | Matson | .......................... 95/46 |
| 5,221,520 A * | 6/1993 | Cornwell | ...................... 422/122 |

(Continued)

FOREIGN PATENT DOCUMENTS

EP    1316357 A1    5/1984

(Continued)

OTHER PUBLICATIONS

D. M. Ruthven, *Principles of Adsorption and Adsorption Processes*, John Wiley and Sons, 1984, New York.

(Continued)

*Primary Examiner*—Frank M Lawrence
(74) *Attorney, Agent, or Firm*—Anne B. Kiernan

(57) ABSTRACT

A process and an apparatus for removal of radon from indoor air. The process having the step of contacting indoor air with an adsorbent, that is a silver-exchanged zeolite. The apparatus for the removal of radon from indoor air comprises a silver exchanged zeolite.

21 Claims, 2 Drawing Sheets

U.S. PATENT DOCUMENTS

| | | |
|---|---|---|
| 5,415,683 A | 5/1995 | Leavitt |
| 5,614,000 A | 3/1997 | Kalbassi et al. |
| 6,036,753 A * | 3/2000 | Appleby et al. .............. 96/108 |
| 6,338,830 B1 | 1/2002 | Moskovitz et al. |
| 6,342,191 B1 | 1/2002 | Kepner et al. |
| 6,432,170 B1 | 8/2002 | Chiang et al. |
| 6,440,196 B1 | 8/2002 | Chiappini et al. |
| 6,658,894 B2 | 12/2003 | Golden et al. |

FOREIGN PATENT DOCUMENTS

| | | |
|---|---|---|
| FR | 2778581 A1 | 11/1999 |
| WO | WO 02/12796 A2 | 2/2002 |

OTHER PUBLICATIONS

S. Charles Scarpitta, Health Physics, vol. 68, No. 3, Mar. 1995, pp. 332-339.

Andrew M. P. McDonnell, Derek Beving, Aijun Wang, Wilfred Chen, Yushan Yan: "Hydrophilic and Antimicrobial Zeolite Coatings for Gravity-Independent Water Separation" Advanced Functional Materials, vol. 15, No. 2, Feb. 2005 pp. 336-340.

* cited by examiner

APPARATUS AND PROCESS FOR AIR CLEANING

BACKGROUND OF THE INVENTION

Poor indoor air quality in homes and office buildings has been recognized as a primary factor which leads to respiratory problems in people. Radon is a primary contributor and levels above four pico-curies per liter (4 pCi/l) have been statistically shown to increase the risk of cancer in individuals. Current EPA efforts are directed to reducing levels of radon below 4 pCi/l and have set target levels of 0.4 pCi/l which is approximately the level in atmospheric air.

Radon gas, which is a radioactive decay by-product of radium, constantly seeps from subterranean radium deposits and out through the surface of the earth's crust, into the atmosphere surrounding the earth. It has a relatively short half-life, in the order of four days. Thus, the radon gas concentration never reaches significant levels upon escaping into the earth's atmosphere. Without confinement, radon gas does not reach sufficient concentration levels, e.g., above 4 pCi/l to pose a human health hazard. When an enclosed structure, such as a building, e.g. a dwelling, or office building, is located in an area of significant radon effluence, as often exists in various parts of the United States, the radon seeps into the structure through cracks or other openings in parts of the foundation, basement or other parts of the building that are in contact or near contact with the earth. If there is an inadequate exchange of interior and exterior air within the building, significant radon concentrations can develop within a building, which are above current governmental limits, e.g., above 4 pCi/l.

There have been significant developments in methods for the detection of radon in an enclosed building or structure and for removal of radon from such building. Representative patents illustrating systems to purify indoor air to remove these various impurities in buildings such as homes, office buildings, etc. include U.S. Pat. Nos. 4,764,187; 4,801,800; 4,849,111; 6,440,196; 6,342,191; 6,338,830; and 6,658,894; all of which are incorporated herein by reference.

BRIEF SUMMARY OF THE INVENTION

This invention provides a process for removal of radon and/or other contaminants from indoor air comprising the step of contacting said indoor air with an adsorbent, said adsorbent comprising a silver-exchanged zeolite.

In another embodiment of the process, other impurities, which may affect respiration, are sometimes present in air within buildings and these include hydrocarbons, CO, $CO_2$, ozone, olefins, nitrogen oxides, sulfur oxides, water and microorganisms. These impurities can be removed, in addition to radon, if present, via a layering of adsorbents that are designed for selective removal of the impurities within the adsorption system. One embodiment provides a process for the removal of impurities from indoor air contaminated with radon of 2 pCi/l or greater within a building comprising the steps of: contacting the indoor air stream with a porous material which releases silver ions upon contact with water for removing bacteria and molds; contacting the indoor air with a desiccant under conditions for removing moisture; and, contacting the indoor air with a silver exchanged zeolite capable of removing radon.

This invention further provides an apparatus for the removal of radon from indoor air comprising a silver exchanged zeolite.

The process and apparatus provide an ability to remove radon from indoor air in buildings; which may be accomplished at generally ambient conditions if desired; and, using an adsorbent having an affinity and capacity for radon.

DETAILED DESCRIPTION OF THE INVENTION

The current invention relates to adsorbent processes and adsorbent apparatuses for removing radon and optionally other impurities from indoor air. The term "indoor air" means air that is inside a building. The term "building" means any enclosed or semi-enclosed structure in which humans or other animals live, visit, or work. The adsorbent process, in one embodiment, may provide for the removal of radon from indoor air which has a level of radon above 2 pCi/l. Although the current EPA standards call for removal of radon at levels of 4 pCi/l and above, levels of 2 pCi/l and above can also be unacceptable.

The adsorption process of the invention employs a silver exchanged zeolite adsorbent as the adsorbent for radon removal, or a silver/lithium exchanged zeolite. It has been found that such silver exchanged zeolites have an improved capacity for radon over carbon adsorbents. Therefore, the present invention relates to an indoor air cleaning apparatus that uses a silver exchanged zeolite for the removal of radon. Silver exchanged zeolites which may be used in the processes and apparatuses of this invention include the A, LSX, Y, mordenite, chabazite, clinoptilite, erionite, ferrierite, zeolite L, and offretite.

Figure 1:
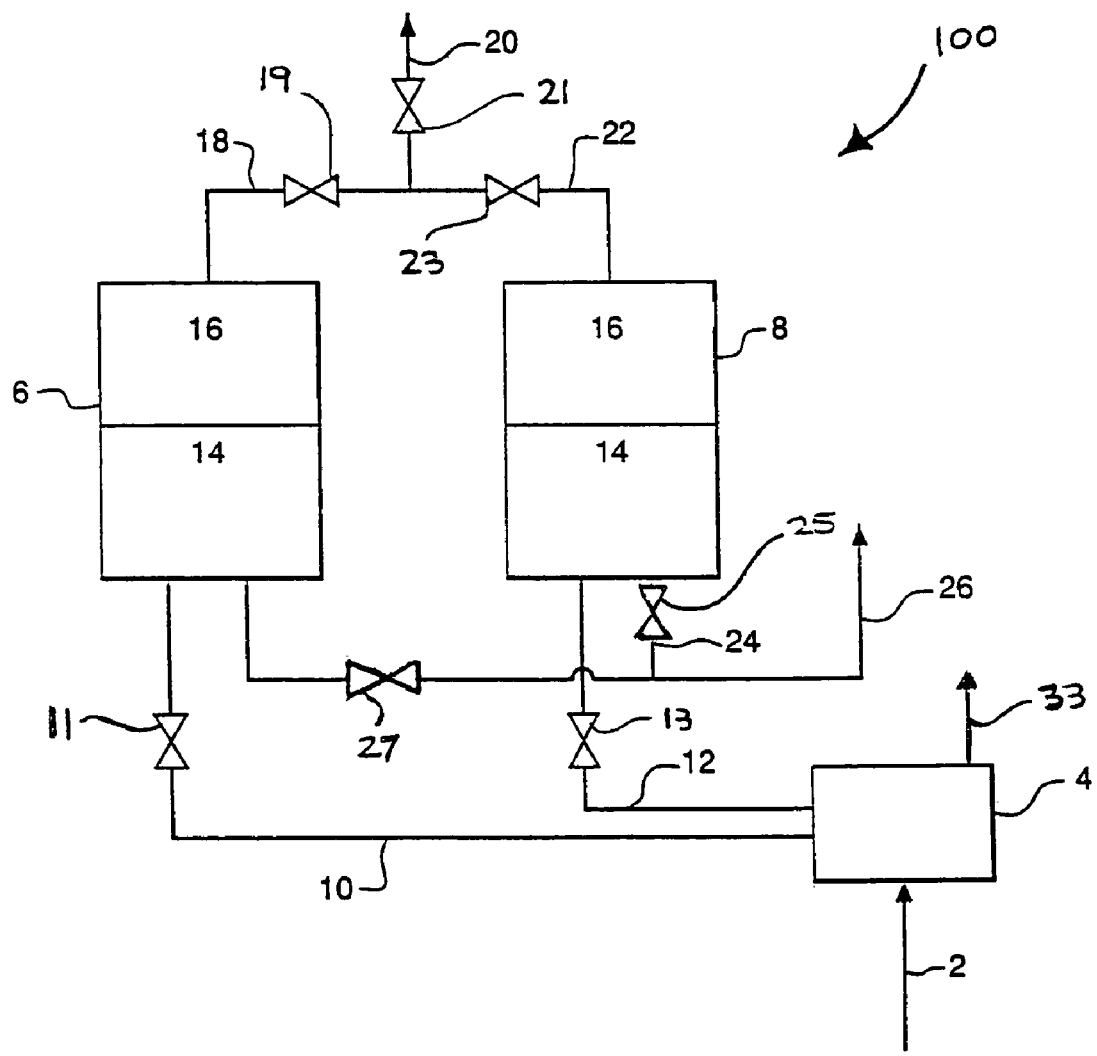
FIG. 1 is a view of a first embodiment of an adsorption apparatus designed to remove radon from indoor air.

To facilitate an understanding of the invention, reference is made to FIG. 1 which shows an apparatus 100 of this invention consisting of two adsorption beds 6 and 8. Any number of beds, typically one to twelve, can be useful in an apparatus of this invention. In the embodiment shown in FIG. 1 indoor air that needs radon removed from it, which may be referred to as "contaminated air" in this description is introduced to the adsorption apparatus via line or pipe 2 by control unit 4. Within control unit 4 may be a fan or a pump or the like that provides the necessary power to force the contaminated air into line 2 through lines 10 and/or 12 and through the adsorption beds 6 and/or 8, and the necessary electronics and other parts (not shown) to control the opening and closing of the valves to run the apparatus and process of this invention. In operation, contaminated air at temperatures that may be from 10 to 40° C., generally from 15 to 30° C., is introduced to either adsorption bed 6 or 8 via lines 10 or 12 at pressures that may range from 1.1 to 10 atm. As an example, in one embodiment of the process of this invention, contaminated air is first introduced to adsorption bed 6 via line 10. In the embodiment shown in FIG. 1, moisture is removed or substantially or partially removed from the Contaminated Air by a first layer of adsorbent 14, such as silica gel or other desiccant to create a low-moisture-content or moisture-free air, which shall be referred to as "moisture-free air". (A separate adsorbent layer to remove moisture is optional to the invention. Water could alternatively be removed, if desired, by chilling the contaminated air, compressing the contaminated air or passing the contaminated air through a polymeric dehydration membrane.)

Radon is substantially or partially removed from the moisture-free air by passing the moisture-free air through the adsorbent layer 16 comprised of the Ag exchanged zeolite to create "cleaned air", which exists bed 6 via lines 18 and 20 and is returned to the indoor air atmosphere. The phrase "cleaned air" describes the air stream that exists the adsorber bed 6 (or 8) via line 20. The cleanliness of the clean air stream is relative to the contaminated air that entered the apparatus 100.

Silver zeolites have been found to have a capacity and retention for adsorbing radon. Examples of silver zeolites useful in this invention are disclosed for example in U.S. Pat. Nos. 4,019,880; 6,432,170; 6,658,894; and 4,911,899, incorporated herein by reference. Crystalline zeolite adsorbents that are useful in this invention may be comprised of a silver-exchanged lithium zeolite having an ion exchange composition of the form $Li_xAg_yM_z$ where $0.85 \leq x+y \leq 1$, $0.2 \leq y \leq 0.7$, $0 \leq z \leq 0.15$ and $x+y+z=1$, with M representing one or more cations, and x, y, and z representing fractions of total exchangeable sites in the zeolite. M can be a cationic form of one or more elements selected from alkaline or alkaline earth metals, rare earths, transition metals, or Group IIIA metals. M preferably is a cationic form of one or more elements selected from the group consisting of Na, K, Cs, Mg, La, Ce, Ca, Al, or Zn. Preferably, the Si/Al ratio is less than or equal to 1.25, and generally about 1. The adsorbents of the invention can be made from a base-type X zeolite (either powder or formed particles), which typically have sodium or sodium/potassium ions as the charge-compensating cation.

In preparing the zeolite, there is a preferred sequential exchange of the cations. First, the sodium or potassium ions, as the case may be, are replaced by lithium cations. Typically, this is effected by contacting the zeolite with an aqueous solution of a lithium salt, e.g., lithium chloride, lithium nitrate, or lithium acetate using known methods. Substantially all of the sodium or potassium ions are replaced to a level of greater than 85%, preferably greater than 94% of exchangeable cations, using various contacting methods which are known in the art. Some of the original cations may remain.

Once the sodium or potassium ions are substantially replaced by the lithium cations, the zeolite is contacted with an aqueous solution of a silver salt, e.g., silver nitrates, acetates, and the like, in either single or multiple contactings thereby replacing a portion of the lithium cations with silver cations. The level of replacement preferably ranges with the silver cations present in an amount from 20 to 70%, more preferably from 30 to 60% and most preferably from 35 to 45% of the replaceable cations for X zeolites. Thus, in the formula, $Li_xAg_yM_z$, where the sum of x+y ranges from 0.85 to 1; the values of y ranges from 0.2 to 0.7, preferably 0.3 to 0.6, or from 0.35 to 0.45; and the values of z ranges from 0.0 to 0.15, or from 0.0 to 0.06.

Once the appropriate level of cation exchange has been effected, the zeolite is dried to bring the water concentration down to about 10 weight % or less. Drying can be accomplished in an oven which is swept preferably with dry, $CO_2$-free air. Heating may be continuous in a slow ramp or by stages, up to a temperature of 250° C., where the sample is held for 2 to several hours until the water concentration is below 10 weight %. It is then calcined at 350 to 450° C., preferably at a temperature of 350 to 400° C., in dry, $CO_2$-free air to bring the water concentration down to less than 1 weight %. Other temperatures may be used outside the range. It is preferred (but not required) to pass dry, $CO_2$-free air through the zeolite adsorbent during calcination.

In the operation of the FIG. 1 embodiment, the radon-free or radon-reduced air, referred to as the "cleaned air" is removed or exits from adsorber bed 6 via line 18 and is released to the building's atmosphere (indoor air) via line 20. In one process of the invention, optionally, while adsorption bed 6 is being used to remove radon from the contaminated air, bed 8 is simultaneously regenerated. Regeneration of bed 8 which is contaminated can be accomplished by, for example: 1) purging the bed with an uncontaminated gas stream, 2) heating the contaminated bed under a flow of uncontaminated gas or 3) lowering the pressure of the contaminated bed typically under a flow of uncontaminated gas. Alternatively, the regeneration step may include a combination of any or all of the just-listed regeneration processes 1, 2 and 3. In one embodiment, with reference to FIG. 1, the uncontaminated gas stream, also called the regenerative gas stream can be a portion of the cleaned air stream provided to bed 8 via line 22 by opening valve 23 and optionally adjusting valves 19, 21, and/or 25. The uncontaminated gas stream will pick up contaminates from bed 8 and become a waste stream that will exit bed 8 via line 24 and be vented to the outdoor air via line 26.

Alternatively or in conjunction with other regeneration steps, to facilitate regeneration of the adsorption beds, e.g., to remove moisture from the adsorbent, the contaminated adsorbent bed 6 or 8 may be closed via valve 19 or 23 and valve 27 or 25, respectively, and vacuum applied to either of the adsorption beds from a vacuum pump (not shown) within control unit 4, via line 10 or 12 and the air with impurities may be vented via vent 33 to the outdoor air (outside atmosphere). Once adsorption bed 8, for example, is regenerated, the process is cycled and contaminated air is introduced to adsorption bed 8 via line 12 for cleaning. Adsorption bed 6 then is regenerated using a portion of the cleaned air from adsorption bed 8 via lines 22 and 18. Regeneration produced waste gas is vented from adsorption bed 6 via line 26.

Other regeneration processes and further descriptions of the regeneration of adsorption beds have been disclosed in the prior art for other adsorption processes and can be adapted to this invention by a person of ordinary skill in the art. Additionally other process steps, such as pressurization, depressurization, and bed equalization steps can be used in the processes and apparatuses of this invention. Patents that disclose the regeneration of adsorption beds and other process steps for adsorption apparatuses include, for example, U.S. Pat. Nos. 3,430,418; 3,564,816; 5,415,683 and 5,614,000, incorporated herein by reference. Additionally, various adsorption processes which can be used are described in detail in *Principles of Adsorption and Adsorption Processes*, D. M. Ruthven, John Wiley and Sons, New York.

The adsorption apparatus and process as shown may operate cyclically, and can use pressure swing adsorption (PSA), vacuum swing adsorption (VSA), thermal swing adsorption (TSA) or a combination. The valves which are shown in the Figures are controlled by the control 4 in order to accomplish the cyclic process. The valves are shown as solenoid or air actuated switching valves, but may be replaced with one or more rotary valves, if desired.

Often, a variety of impurities may be found in the air within buildings. These too, can cause respiratory problems, such impurities include bacteria, hydrocarbons, volatile organics, carbon monoxide, formaldehyde, ozone, particles, molds, etc. An apparatus and process to clean the indoor air to remove these various impurities would be beneficial. The apparatus shown in FIG. 1 can be used for this purpose or one or more adsorbents can be added to the adsorption system of FIG. 1 to remove additional impurities from the indoor air. One such embodiment of this invention having multiple additional layers for the removal of additional impurities is shown in FIG. 2.

Figure 2:
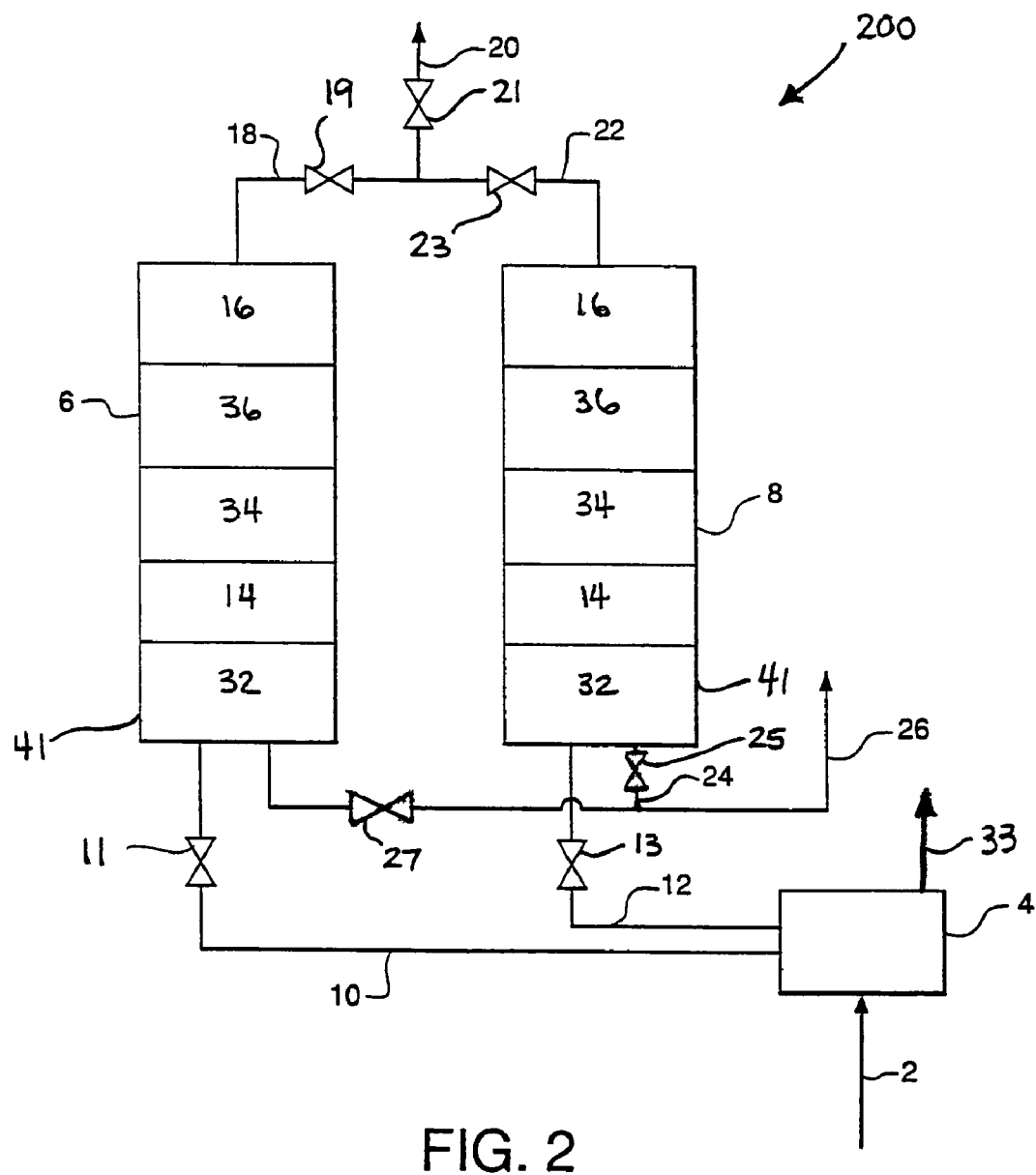
FIG. 2 is a second embodiment of an adsorption apparatus for the removal of radon and other impurities from indoor air.

In the embodiment shown in FIG. 2, the adsorption apparatus 200 consists of 2 adsorption beds 6 and 8; however, alternative apparatuses of this invention may comprise any number of beds. (Where there are similar components to that of FIG. 1, identical numbering has been used.) Each bed is designed to remove various impurities from the contaminated indoor air which enters the beds 6 and 8 via line 2. The adsorption beds 6, 8 contain layers of different adsorbents. The initial adsorbent layer 32 may consist of any porous material which will release silver ions upon contact with water, for example, a silver exchanged zeolite. This layer is preferably located at or near the inlet end 41 of the adsorption beds 6 and 8 to increase the beds' effectiveness in the removal of microorganisms, such as, bacteria, viruses, molds and fungi. When located at or near the inlet 41, or prior to a dessicant layer, the silver exchanged zeolite (for example) may become hydrated by adsorbing moisture from the contaminated air. When hydrated, the silver ions in adsorbent layer 32 remove microorganisms from the contaminated air, thereby producing a de-bugged contaminated air stream.

In the embodiment shown in FIG. 2, the second adsorbent layer 14 comprises a desiccant in sufficient amount to remove water from the contaminated air stream. Typical desiccants include alumina, silica gel, zeolites, alumina/zeolite composites, etc. The water is removed from the contaminated air stream by the dessicant, so that the additional adsorbent layers remain in suitable form for removal of other impurities, otherwise the one or more of the other adsorbent layers might preferentially adsorb the water instead of impurities. For example, the contaminated air should be relatively free of moisture when it contacts the silver exchanged zeolites in adsorbent layer 16 for the silver exchanged zeolites to be more effective for the removal of radon.

The third adsorbent layer 34 may comprise an adsorbent for the removal of hydrocarbons and volatile organics such as formaldehyde, benzene, acetone, vinyl chloride, methanol, methyl ethyl ketone, etc, if present. Typical adsorbents useful in this layer include at least one of the following: activated carbon, silica gel, alumina and high Si/Al ratio zeolites (like silicalite). It is preferred that this adsorbent layer is comprised of an adsorbent other than the type of adsorbent employed to remove water, although they can be the same, e.g., silica gel or alumina.

The fourth adsorbent layer 36 as shown in the adsorber system may comprise an adsorbent or catalyst that can decompose ozone. Typical materials for the removal of ozone include hopcalite (CuO/MnO mixture), noble metal catalysts and various adsorbents including activated carbon, zeolites, silica gel, hydrotalcite, clays and alumina.

The fifth adsorbent layer 16, as shown in FIG. 2 in adsorption beds 6 and 8 may be the silver exchanged zeolite. By removing most or substantially all of the impurities in the air stream prior to removal of radon, the effectiveness of the silver exchanged zeolite for removal of radon is enhanced. Alternatively, the order of the layers in the adsorption system may be rearranged if desired. Both beds in each embodiment are the same, although that is not required.

The layered beds 6 or 8 remain on feed (e.g. contaminated air is pumped into the bed) until at least one of the adsorbents in adsorbent bed 6 or 8 is saturated with impurities. Once the bed is saturated, it must be regenerated either by purging, heating or evacuation or a combination of all three. The thermal swing technique may be used to regenerate a contaminated bed of the apparatus 200. Heated, uncontaminated air, typically effluent (cleaned air) from a bed that is cleaning the contaminated air (the on-line bed), is passed through the contaminated bed at temperatures high enough to desorb the unwanted impurities. Typically, then the bed is cooled back down to the feed temperature by turning off the heater (not shown) that is used for heating the uncontaminated air used as the regeneration gas.

When the apparatus and process shown in FIG. 2 are operating properly, the effluent (cleaned air) in line 18 or 22 in FIG. 2 is relatively clean in that substantially all or most of the trace impurities in the air have been removed. The cleaned air is then released to the indoor air via pipe 20. Optionally the process and apparatus of this invention may additionally provide that the clean air may be hydrated by a humidifying device that may be added to or after line 20 to add humidity to the clean air to compensate for the loss of water in the adsorption process. As discussed above for FIG. 1, a portion of the cleaned air from the on-line adsorption unit may be used via pipes 18 and 22 to regenerate the adsorbent bed 6 or 8 that is not on line, and then that waste air which will desorb impurities from the adsorbents should be vented externally to the building via pipes 26 or 33. Typically, the feed temperature of the contaminated air into bed 6 or 8 may be from 0 to 50° C.; the regeneration temperature may be from 50 to 250° C.; the feed pressure may be from 1 to 10 bara; the feed flow rates may be from 10 to 2000 SCFH, the regeneration pressure may be from 0.05 to 3 bara; and the total cycle times may be from 10 seconds to 24 hours. Additionally, the typical particle size for the adsorbent materials may range from 0.5 to 5 mm in diameter.

If the embodiment comprises a thermal swing process step for regenerating the adsorption beds, preferably in a process that alternates heating the beds, adsorption bed 6 or 8 is heated to temperatures of 50 to 250° C., and then cooled back down to ambient temperature to ready the just-regenerated bed for the next adsorption cycle. Typical on-line (adsorption times) are 30 minutes to 8 hours. If the 2-bed system shown in FIG. 2 is operated in a cyclic manner with one bed on-line while the other bed is regenerated, then a portion of the air in a building is continually being cleaned. Alternatively, the process may be operated so that one or more beds or all of the beds in the adsorption apparatus of this invention are on-line and then one or more or all of the beds are regenerated, if desired. The embodiment of the apparatus shown in FIG. 2 is capable of removing the following impurities from contaminated indoor air: radon, water, CO, $CO_2$, volatile hydrocarbons, olefins, bacteria, virus, fungus, particles, $SO_2$, $NO_2$ and ozone.

One of the benefits associated with the use of a silver exchanged zeolite for the removal of radon is that the radon need not be removed from the zeolite, i.e., the capacity is such that adsorption canisters housing the adsorption beds for radon removal can last for years. In addition, because of the high affinity for the radon, regeneration of the adsorption beds can be accomplished using the conditions associated with the removal of moisture and impurities from the beds, e.g. vacuum regeneration, and the adsorbed radon may not be disturbed.

The described embodiments above and examples below are only exemplary. Additional or fewer layers can be used if desired, or the same layers in a different order in apparatuses and processes of this invention. Additionally, the beds in the apparatuses of the figures are shown having the same layers in the same order in the beds of each apparatus, but that is not required. The beds of a single apparatus may consist of different layers and/or the same layers in a different order.

The following examples are preferred to illustrate the effectiveness of the adsorbents in the air cleaning processes and apparatuses of this invention.

EXAMPLE 1

Effectiveness of AgLi X Zeolite for Radon Removal

The adsorption of radon was monitored by passing 140 $Nm^3$ of dry air per hour through an adsorption vessel at 30° C. that contained 340 kgs of a zeolite. The particular zeolite used was an X zeolite with 20% of its ion exchange capacity occupied by Ag+ ions and 80% occupied by Li+ ions. The zeolite was manufactured by Zeochem, Inc. using the ion exchange of silver into LiX zeolite. After 84 hours of operation, no radon breakthrough was detected. The minimum radon capacity calculated from this test is 140 $Nm^3$/hr×84 hours×1/340 kgs=34.6 $Nm^3$/kg of adsorbent. The capacity of activated carbon for radon quoted by Scarpitta (Health Physics, Volume 68, Number 3, March 1995, pp 332-339) is 3.7 $Nm^3$/kg of carbon at 30° C. and 0% RH. The results of this test show that the equilibrium capacity of AgLiX zeolite is at least about 10 times greater than that for the industry standard radon adsorbent, activated carbon.

EXAMPLE 2

Removal of Carbon Monoxide Using Silver Exchanged Zeolite

Another air impurity, which is known to cause respiratory problems, is carbon monoxide. To determine the effectiveness of the silver exchanged zeolites for carbon monoxide removal, the adsorption of carbon monoxide was measured on the AgLiX zeolite employed in Example 1. Adsorption isotherms were compared with that for BPL activated carbon from Calgon, Inc. The results clearly show that the AgLiX material has significantly higher CO capacity than activated carbon at low CO partial pressure. The initial CO isotherm slopes (Henry's Law constants) for AgLiX and activated carbon are 357 and 0.58 mmole/g/atm, respectively. The AgLiX material has over a 600 times greater capacity at low CO partial pressure than the activated carbon.

The CO capacity of AgLiX is high enough to use this material for (cyclic) removal of CO from indoor air in an apparatus or process of this invention. If the feed pressure to the adsorptive air cleaner is 2 atm and the CO concentration in the air is 10 ppm, then the CO partial pressure is $1\times10^{-5}$ atm. The CO capacity from Henry's constant is 357 mmole/g/atm×0.00001 atm=$3.6\times10^{-3}$ mmole CO/g. Each $Nm^3$ of air would contain $4.4\times10^{-4}$ gmole of CO. Therefore, each kg of AgLiX can treat 8.2 $Nm^3$ of air (1 $Nm^3$/0.00044 gmole× 0.0036 gmole/kg). This capacity is quite high, even higher than that for radon on activated carbon. Conversely, the capacity of activated carbon is much too low to be useful (0.013 $Nm^3$/kg of carbon) for the removal of CO from air.

EXAMPLE 3

Adsorption of Carbon Monoxide Using CaX Zeolite 40 grams of CaX from LaPorte Industries was ion exchanged with 1 liter of 0.1N $AgNO_3$ at 25° C. for 16 hours. After ion exchange the samples were washed with 8 liters of distilled water. The adsorption of CO was measured on the untreated and ion-exchanged samples at 30° C. after the samples were thermally regenerated in flowing $N_2$ at 400° C. for 12 hours. The Henry's Law constants and selectivities are given in the table below:

| Adsorbent | (mmole/g/atm) $K_HCO$ | (mmole/g/atm) $K_HN_2$ | $S_H$ |
|---|---|---|---|
| CaX | 18.2 | 1.5 | 12.1 |
| Ag/CaX | 125.0 | 0.3 | 416.7 |

The results show that exchange of $Ag^+$ in CaX zeolite produces an adsorbent with the properties required for trace CO removal, i.e., 1) high $CO/N_2$ selectivity and 2) high CO capacity at low CO partial pressure. This example shows that the silver exchanged zeolite does not have to have lithium co-ions to demonstrate high carbon monoxide capacity, and is useful in an apparatus or process of this invention for that purpose.

EXAMPLE 4

Removal of Ozone

The ability of hopcalite ($CuO/MnO_2$ termed Carulite from Carus Corporation) to decompose ozone was determined at 25° C. With a feed composition of 5 mole % ozone in air and flow rate of 750 cc/min (0.8 second contact time), 10 grams of Carulite was able to reduce the ozone concentration below 1 ppm. This corresponds to an ozone conversion of 99.999%. This example shows that a layer of hopcalite in the adsorption bed will be very effective in removing ozone from contaminated air in the apparatus or process of this invention.

EXAMPLE 5

Removal of Ozone Using Carbon

The ability of activated carbon (type BPL from Calgon) to remove ozone from an air stream was also measured. Using a TGA apparatus, the weight gain of activated carbon was measured at 25° C. with a gas stream containing 0.1 mole % ozone in oxygen (100 cc/min). The weight gain of the carbon after exposure to the ozone-containing stream after 3 days was 18 wt %. The Henry's law constant for ozone adsorption derived from this experiment was 3750 mmole/g/atm. This result shows that activated carbon has a large capacity for ozone, and can be used in the apparatus or process of this invention for removing ozone from contaminated air.

EXAMPLE 6

Removal of Nitrogen Oxides

The ability of a high silica/alumina ratio zeolite to adsorb $NO_2$ was tested at 25° C. The adsorption of $NO_2$ from air was measured on a TGA on H-mordenite (UOP, LZM-8) using a feed stream of 200 ppm $NO_2$ in air with a flow rate of 100 cc/min. The resulting weight increase of the zeolite was 2.8 wt %. The corresponding Henry's law constant derived from this data is 3044 mmole/g/atm. This result shows that zeolites have a very high capacity for $NO_2$. It is expected that zeolites also have a very high capacity for $SO_2$ and hydrocarbons as well. Thus, a layer of high Si/Al ratio zeolite in the adsorption bed will be effective for the removal of hydrocarbons, sulfur oxides and nitrogen oxides.

EXAMPLE 7

Removal of Formaldehyde

The adsorption of formaldehyde was measured on activated carbon, BPL carbon at 25° C. by monitoring the breakthrough of formaldehyde from a stream consisting of 1000 ppm formaldehyde in He. The equilibrium capacity determined by breakthrough was 0.86 wt %. This corresponds to a Henry's law constant of 287 mmole/g/atm. Activated carbon shows the high capacity required for removal of formaldehyde from air. Thus, a layer of activated carbon in an adsorption bed of an apparatus of this invention will effectively remove formaldehyde from contaminated air.

EXAMPLE 8

Regeneration of Silver Exchanged Zeolite Having Adsorbed Radon Therein

A small bed of 20% AgLiX zeolite (30 grams) was put on a partially dried ambient air feed for 72 hrs with 600 cc/min airflow. After the completion of the run the bed was split and half was regenerated at 150° C. in a $N_2$ flow for 16 hrs. The samples were sent out for radiological evaluation for radon upon completion of the regeneration. Results for the samples show that the radon capacity of the unregenerated material was measured to be 5462 pCi/g. That value is about 30 times higher than that for activated carbon, the current industry standard for radon adsorption. The sample when regenerated at 150° C. showed a residual radon loading of 5.4 pCi/g, thus indicating that radon could be thermally regenerated from AgLiX at 150° C.

EXAMPLE 9

Biocide Activity of Silver Exchanged Zeolite

The biocide properties of 20% AgLiX were tested against the following microorganisms:

Test Microorganisms:
*Aeromonas hydrophilia, Alcaligenes faecalis, Corynebacterium ammoniagenes, Enterobacter aerogenes, Escherichia coli, Klebsiella pneumoniae, Pseudomonas aeruginosa, Proteus vulgaris, Providencia rettgeri, Pseudomonas stutzeri, Shewanella putrefaciens, Serratia liquefaciens, Acinetobacter baumannii, Burkholderia cepacia, Chryseobacterium meningosepticum, Sphingobacterium spiritivorum, Ralstonia pickettii*, and *Gluconoacetobacter liquefaciens*.

Mixed Bacterial Pool Inoculum Preparation:
Each bacterial culture was individually grown on nutrient agar slants, except *Gluconoacetobacter liquefaciens* was grown on potato dextrose agar slants, by inoculating the agar surfaces. The nutrient agar slants were incubated for 24-48 hours at 30° C. and the potato dextrose agar slants were incubated for 48-72 hours at 25° C. After this incubation period, the cells were harvested using quarter strength Ringers solution to wash the bacterial colonies off the agar surface. The washings from all of the slants were combined into one sterile, Erlenmeyer flask. The number of slants and the amount of Ringers Solution used to wash off the bacterial colonies was adjusted during the procedure to obtain a final mixed microbial viable count in the range of $10^5$-$10^6$ CFU/mL.

Specified amounts of 20% AgLiX were added to nutrient broth (total sample weight equaled 50 g). The resulting samples were then inoculated with 1.0 mL of the mixed bacterial inoculum. After mixing well, an aliquot (5 g) of each test sample was placed into separate Rapid Automated Bacterial Impedance Technique (RABIT) indirect conductivity tubes. The indirect conductivity tubes were then placed into RABIT incubator modules set at 30° C. and the conductivity changes monitored for up to 72 hours. The remainder of each test sample was stored in a 30° C. incubator during the RABIT monitoring period. At the completion of the RABIT monitoring period, the aliquot samples were placed back into their respective sample containers. Each test sample was then re-inoculated with a freshly prepared mixed bacterial inoculum. After mixing well, an aliquot (5 g) of each test sample was again placed into fresh RABIT indirect conductivity tubes and monitored on the RABIT as before. This inoculation and RABIT conductivity monitoring procedure was conducted a total of three times.

The results showed that the silver exchanged zeolites have biocide activity when in hydrated form.

The invention claimed is:

1. A process for removal of radon from indoor air comprising the step of contacting said indoor air with adsorbent, said adsorbent comprising a silver-exchanged zeolite.

2. The process of claim 1 wherein the radon level within said indoor air is at least 2 pCi/l.

3. The process of claim 1 wherein the radon level within said indoor air is at least 4 pCi/l.

4. The process of claim 1 further comprising the step of removing moisture from said indoor air prior to said contacting step.

5. The process of claim 1 wherein the zeolite is selected from the group consisting of zeolite A, zeolite X, zeolite LSX, zeolite Y, mordenite, chabazite, clinoptilite, erionite, ferrierite, zeolite L and offretite.

6. The process of claim 1 wherein the silver-exchanged zeolite is also exchanged with lithium.

7. The process of claim 1 wherein the silver-exchanged zeolite is silver/lithium-exchanged zeolite having an ion exchange composition of the form $Li_xAg_yM_z$ where $0.85 \leq x+y \leq 1$, $0.2 \leq y \leq 0.7$, and $0 \leq z \leq 0.15$ with M representing one or more cations, and x, y, and z representing fractions of total exchangeable sites in the zeolite.

8. The process of claim 7 wherein M is a cationic form of one or more elements selected from the group consisting of Na, K, Cs, Mg, La, Ce, Ca, Al, and Zn.

9. The process of claim 7 wherein the zeolite is zeolite X.

10. The process of claim 4 wherein said step of removing said moisture from said indoor air is performed by contacting said indoor air with adsorbent.

11. The process of claim 10 wherein said adsorbent for said removing step is alumina, silica gel, zeolite or mixtures thereof.

12. A process for the removal of impurities from indoor air contaminated with radon within a building comprising the steps of;
  contacting the indoor air steam with porous material which releases silver ions upon contact with water for removing bacteria and molds;
  contacting the indoor air with desiccant under conditions for removing moisture; and,
  contacting the indoor air with silver exchanged zeolite capable of removing radon.

13. The process of claim 12 further comprising the step of contacting the indoor air with adsorbent capable of removing ozone after said contacting with said dessicant step.

14. The process of claim 13 further comprising the step of contacting the indoor air with adsorbent capable of removing volatile organics or carbon oxides prior to said contacting step for removing radon.

15. The process of claim 14, wherein the silver exchanged zeolite for removing radon is selected from the group consisting of zeolite A, zeolite X, zeolite LSX, zeolite Y, mordenite, chabazite, clinoptilite, erionite, ferrierite, zeolite L, and offretite.

16. The process of claim 14 wherein the silver exchanged zeolite for removing radon is also exchanged with lithium.

17. The process of claim 1 further comprising the step of contacting said air with adsorbent capable of removing hydrocarbons from said air prior to said contacting said silver-exchanged zeolite.

18. The process of claim 1 further comprising the step of contacting said air with adsorbent capable of removing ozone from said air prior to said contacting said silver-exchanged zeolite.

19. The process of claim 1 further comprising prior to said contacting of said silver-exchanged zeolite step, the steps of:
  contacting said air with adsorbent capable of removing moisture from said air, contacting said air with adsorbent capable of removing hydrocarbons from said air, and contacting said air with adsorbent capable of removing ozone from said air.

20. The process of claim 1 further comprising prior to said contacting of said silver-exchanged zeolite step, the steps of:
  contacting said air with adsorbent for removing moisture from said air comprising a material selected from the group consisting of alumina, silica gel, zeolite and mixtures thereof;
  contacting said air with adsorbent for removing hydrocarbons from said air comprising a material selected from the group consisting of activated carbon, silica gel, alumina and high Si/Al ratio zeolites; and
  contacting said air with adsorbent comprising a material selected from the group consisting of hopcalite (CuO/MnO mixture), noble metal catalysts, activated carbon, zeolites, silica gel, hydrotalcite, clays and alumina for removing ozone from said air.

21. The process of claim 20 further wherein the silver-exchanged zeolite for removal of said radon is silver/lithium-exchanged zeolite having an ion exchange composition of the form $Li_xAg_yM_z$ where $0.85 \leq x+y \leq 1$, $0.2 \leq y \leq 0.7$, and $0 \leq z \leq 0.15$ with M representing one or more cations, and x, y, and z representing fractions of total exchangeable sites in the zeolite.

* * * * *

UNITED STATES PATENT AND TRADEMARK OFFICE
CERTIFICATE OF CORRECTION

PATENT NO.        : 7,381,244 B2                                      Page 1 of 1
APPLICATION NO.   : 11/196070
DATED             : June 3, 2008
INVENTOR(S)       : Daniel W. Tyndall et al.

It is certified that error appears in the above-identified patent and that said Letters Patent is hereby corrected as shown below:

Column 11, Line 4;

In claim 12 delete the word "steam" and insert the word -- stream --

Signed and Sealed this

Fifth Day of August, 2008

JON W. DUDAS
*Director of the United States Patent and Trademark Office*